United States Patent
Colon-Cruz et al.

(10) Patent No.: US 7,019,009 B2
(45) Date of Patent: Mar. 28, 2006

(54) ACYL DERIVATIVES OF 5-(2-(4-(1,2 BENZISOTHIAZOLE-3-YL)-1-PIPERAZINYL) ETHYL)-6-CHLORO-1,3-DIHYDRO-2H-INDOL-2-ONE HAVING NEUROLEPTIC ACTIVITY

(75) Inventors: Roberto Colon-Cruz, Groton, CT (US); Timothy Norris, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 267 days.

(21) Appl. No.: 10/689,773

(22) Filed: Oct. 21, 2003

(65) Prior Publication Data

US 2004/0138232 A1 Jul. 15, 2004

Related U.S. Application Data

(60) Provisional application No. 60/420,843, filed on Oct. 24, 2002.

(51) Int. Cl.
*A61K 31/496* (2006.01)
*C07D 417/14* (2006.01)

(52) U.S. Cl. .................... 514/254.04; 544/368
(58) Field of Classification Search ........... 544/368; 514/254.04
See application file for complete search history.

(56) References Cited

U.S. PATENT DOCUMENTS

| 5,206,366 A | 4/1993 | Bowles ................ 544/284 |
| 5,312,925 A | 5/1994 | Allen et al. ............ 544/368 |
| 5,935,960 A | 8/1999 | Walinsky et al. ........ 514/253 |

FOREIGN PATENT DOCUMENTS

| EP | 0790236 | 8/1997 |
| WO | 0010975 | 3/2000 |

OTHER PUBLICATIONS

Hans Bundgaard; Elsevier Science Publishers B.V.; Design of prodrugs: Bioreversible derivatives for various functional groups and chemical entities; (1985); p. 1–10.

Davis, et al.; CNS Drugs; Ziprazidone; (1997) vol. 8. No. 2; p. 153–159.

Caley, et al.; The Annals of Pharmacotherapy; Ziprasidone: The Atypical Antipsychotic; (2002) vol. 36, No. 5; p. 839–851.

*Primary Examiner*—Emily Bernhardt
(74) *Attorney, Agent, or Firm*—Steven T. Zelson; Kristina L. Konstas

(57) ABSTRACT

A process for preparing acyl derivatives as prodrugs of 5-(2-(4-(1,2 benzisothiazole-3-yl)-1-piperazinyl)ethyl-6-chloro-1,3-dihydro-2H-indol-2-one and pharmaceutically acceptable acid addition salts and methods of use as an antipsychotic.

27 Claims, No Drawings

ACYL DERIVATIVES OF 5-(2-(4-(1,2 BENZISOTHIAZOLE-3-YL)-1-PIPERAZINYL) ETHYL)-6-CHLORO-1,3-DIHYDRO-2H-INDOL-2-ONE HAVING NEUROLEPTIC ACTIVITY

This application claims benefit of 60/420,843 filed Oct. 24, 2002.

BACKGROUND

This invention relates to prodrugs which are acyl derivatives of the compound 5-(2-(4-(1,2 benzisothiazol-3-yl)-1-piperazinyl)ethyl)-6-chloro-1,3-dihydro-2H-indol-2-one (hereinafter referred to as ziprasidone), pharmaceutically acceptable acid addition salts thereof, a process for their preparation and a method for their use. Compounds of the invention have neuroleptic activity and are therefore useful as antipsychotics.

U.S. Pat. No. 5,935,960, discloses the compound 1-[2-(6-chloro-2,3,dihydro-2-oxo-1H-indol-5-yl)ethyl]-4-[imino(2-mercaptophenyl)methyl]piperazine as a pro-drug of ziprasidone.

U.S. Pat. No. 5,312,925, discloses the monohydrate hydrochloride salt of ziprasidone, a process for its preparation, pharmaceutical compositions thereof and a method of treating psychotic disorders.

U.S. Pat. No. 5,206,366, discloses an aqueous based process for preparing ziprasidone. Each of the aforementioned United States Patents is hereby incorporated by reference in its entirety.

SUMMARY OF THE INVENTION

The present invention relates to a novel compound of the formula

I

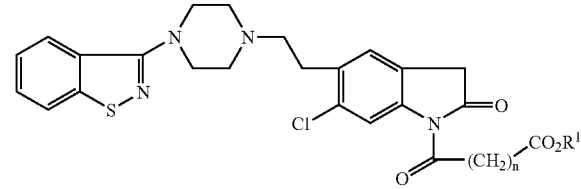

and pharmaceutically acceptable acid addition salts thereof, wherein $R^1$ is selected from the group consisting of hydrogen, methyl, ethyl, n-propyl, iso-propyl, n-butyl, sec-butyl, tert-butyl, 1-pentyl, 2-pentyl, 3-pentyl, n-hexyl, n-heptyl, n-octyl, n-nonyl, n-decyl and n is an integer of 1 to 5.

Preferred pharmaceutically acceptable acid addition salts of a compound of formula I are selected from the group consisting of chloride, mesylate, acetate, fumarate, succinate, maleate, besylate, citrate, tartrate, and sulfate. The most preferred salt is the hydrochloride salt.

A preferred subgroup of compound I is the subgroup wherein $R^1$ is selected from the group consisting of methyl, ethyl, iso-butyl and decyl and n is 2.

The most preferred compound which may be prepared in accordance with the present invention is 4-{5[2-(4-benzo[d]isothiazol-3-yl-piperazin-1-yl)ethyl]-6-chloro-2-oxo-2,3-dihydro-indol-1-yl}-4-oxo-butyric acid ethyl ester, hydrochloride salt.

The present invention also relates to a process for preparing a compound of the formula

I

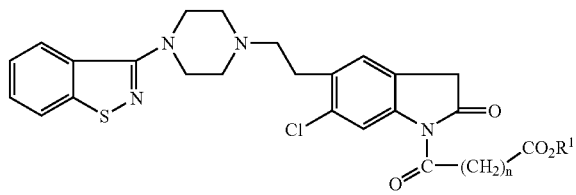

comprising reacting a compound of the formula

II

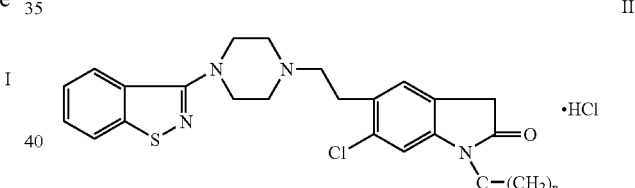

with a base. According to the invention, a compound of the formula II may be prepared by reacting a compound of the formula

III

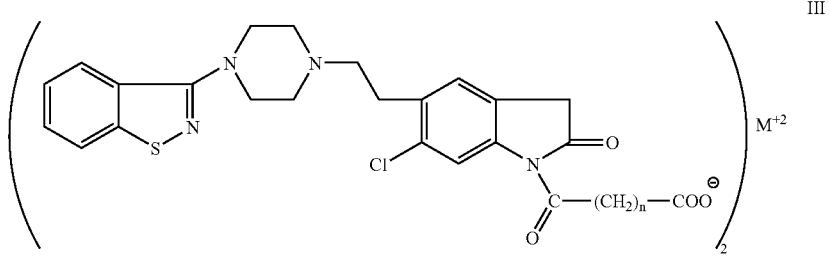

with an alcohol of formula R¹—OH in the presence of concentrated hydrochloric acid wherein M is Ba or Ca; and R¹ is selected from the group consisting of hydrogen, and $C_1$ to $C_{10}$ alkyl.

According to the invention, compound III may be prepared by reacting a compound of the formula

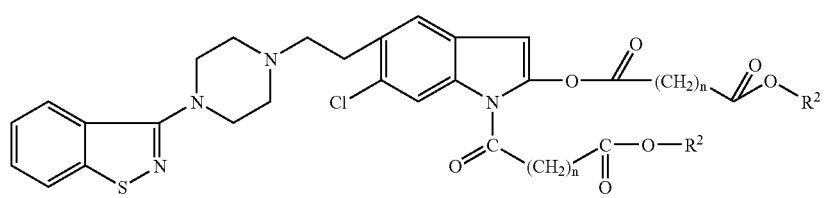

wherein $R^2$ is $C_1$–$C_{10}$alkyl and n is an integer of 1 to 10, with an inorganic base having the formula $M(OH)_2$. M is Ba or Ca.

According to the invention, the compound of formula IV may be prepared by reacting a compound of the formula

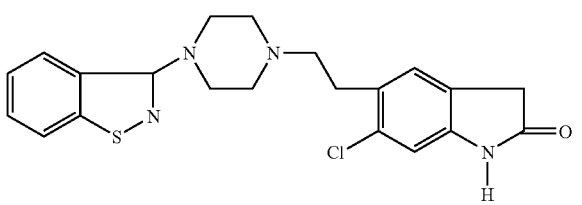

with an anhydride acylating agent having the formula $R^2O_2C$—$(CH_2)_n$—$C(=O)$—$O$—$C(=O)$—$(CH_2)_n CO_2R^2$ wherein $R^2$ is $C_1$–$C_{10}$ alkyl and n is 1–5.

In the process for preparing compounds of formula I, the preferred base is selected from the group consisting of alkali metal bicarbonates, alkali metal, carbonates, tertiary amines such as C-1 to C-6 trialkylamines, and heterocyclic weak bases such as pyridine, lutidine or picoline. The most preferred base is an aqueous solution of sodium bicarbonate.

$R^1$ in the alcohol $R^1$—OH is selected from the group consisting of alkyl C-1 to C-10. A preferred $R^1$ in the alcohol $R^1$—OH is selected from the group consisting of methyl, ethyl and iso-butyl. In the most preferred embodiment $R^1$ is ethyl.

The hydrolytic conversion of the di-acylated compound having the formula IV into the mono-acylated alkaline earth metal salt of formula III is conducted at elevated temperature in the presence of an alkaline earth metal hydroxide in water and an inert water miscible organic solvent. The preferred alkaline earth metal hydroxides are calcium hydroxide or barium hydroxide. The preferred temperature is from about 45° C. to about 80° C. and the preferred solvent is selected from the group consisting of tetrahydrofuran, dioxane, dimethylsulfoxide, alkyl ethers, N,N-dimethylformamide and other aprotic solvents or ethers with boiling points in the range of about 50° C. to 200° C. The most preferred solvent is tetrahydrofuran.

Barium or calcium salts having the formula III are useful intermediates in the preparation of the acyl derivatives of the present invention. In a preferred embodiment where n is 2 the acyl derivative is the succinyl derivative and the salt is the calcium salt.

4-{5-[2-(4-benzo[d]isothiazol-3-yl-piperazin-1-yl) ethyl]-6-chloro-2-oxo-2,3-dihydro-indol-1-yl}-4-oxo-butyric acid barium salt, In a most preferred embodiment, the compound having formula III is 4-{5-[2-(-benzo[d]isothiazol-3-yl-piperzin-1-yl)ethyl]-6-chloro-2-oxo-2,3-dihydroindol-1-yl}-4-oxo-butyric acid calcium salt.

Compounds of formula IV are useful intermediates in the preparation of the acyl derivatives of the present invention. Preferably n is 2 and $R^1$ is $C_2$–$C_4$alkyl.

In a most preferred embodiment, the compound having formula IV is succinic acid 5-[2-(4-benzo[d]isothiazol-3-yl-piperazin-1-yl) ethyl]-6-chloro-1-(3-ethoxycarbonyl-propionyl)-1H-indoyl-2-yl ester ethyl ester.

The inorganic base $M(OH)_2$ reacts with compound IV in a water miscible organic solvent preferably tetrahydrofuran.

A preferred base having formula $M(OH)_2$ is the base wherein M is Ca or Ba. The most preferred base is calcium hydroxide.

The preferred acylating agent is an aliphatic anhydride acylating agent of formula

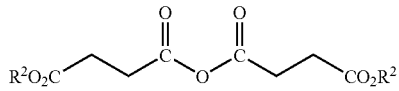

wherein $R^2$ is ethyl.

The acylation is conducted in anhydrous methylene chloride in the presence of an organic base and a diethyl ether adduct of magnesium bromide.

In a preferred embodiment the organic base is triethylamine.

The effective dosage for ziprasidone pro-drugs of the present invention depends on the intended route of administration, the indications to be treated, and other factors such as age and weight of the subject. In the following dosage ranges, the term "mgA" refers to milligrams of the free base of the pro-drug. A recommended range for oral dosing is 6 to 400 mgA/day, preferably 50 to 250 mgA/day, more preferably 50 to 100 mgA/day. A recommended range for parenteral administration, such as injection is 3.0 mgA/day to 200 mgA/day and preferably 6.0 to 100 mgA/day.

DETAILED DESCRIPTION OF THE INVENTION

Acyl derivative of ziprasidone are synthesized by a process shown in Scheme 1 below. $R^1$, and $R^2$, and n in Scheme 1 are defined above in reference to formula I, II, and IV. The metal ion $M^{+2}$ with reference to formula III is $Ca^{+2}$ or $Ba^{+2}$.

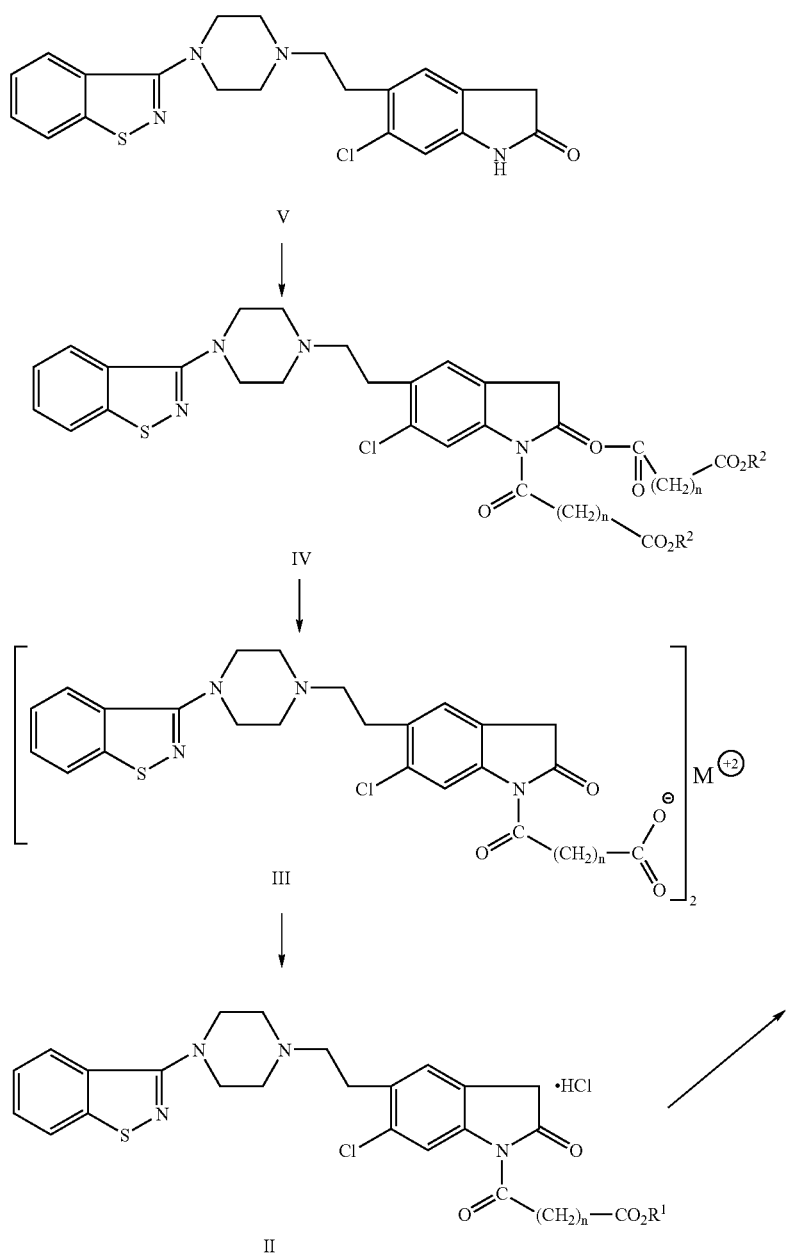

SCHEME 1

Ziprasidone (V) is acylated at both the 1-nitrogen and 2-oxo position (of the indole ring) with acyl anhydride VI in the presence of magnesium bromide diethyl etherate adduct and triethylamine under completely anhydrous conditions according to the method of Yamada et al., Tetrahedron Letters, 43, 647, (2002). It was surprising to obtain the diacylated product using this method since the acylation of oxindole with pivalic anhydride according to Yamada produced only mono-substitution at either the H or O atom.

The anhydride used in the acylation reaction is prepared according to Scheme 2.

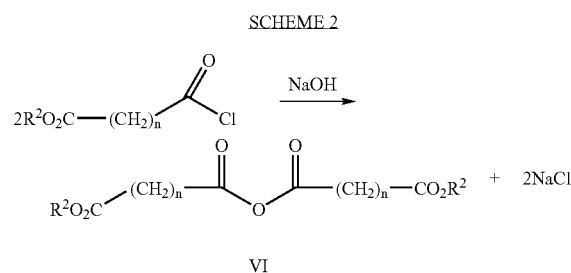

SCHEME 2

According to Scheme 2, a selected acyl chloride is self-condensed forming the desired anhydride by reaction with sodium hydroxide pellets in anhydrous methylene chloride. The acylation step in Scheme 1 is carried out in two separate addition steps. The anhydride solution in methylene chloride was added to a previously prepared solution made from combination of ziprasidone solution in anhydrous tetrahydrofuran and a solution of magnesium bromide diethyl etherate adduct (MgBr$_2$.Et$_2$O) and triethylamine in anhydrous dichloromethane under nitrogen. The reaction temperature was controlled to a range of between about 0° C. and about 25° C.

The corresponding diacylated product IV was then hydrolyzed with either calcium or barium hydroxide in aqueous tetrahydrofuran to selectively remove the acyl group at the 2-oxo position and hydrolyze the remaining ester to yield the corresponding calcium or barium salt (III) which was isolated by filtration.

The compounds of formula III wherein $M^{+2}$ is the Ca or Ba cation are novel compounds, which may be hydrolyzed under selected conditions to give compounds II, VI, or VII according to Scheme 3.

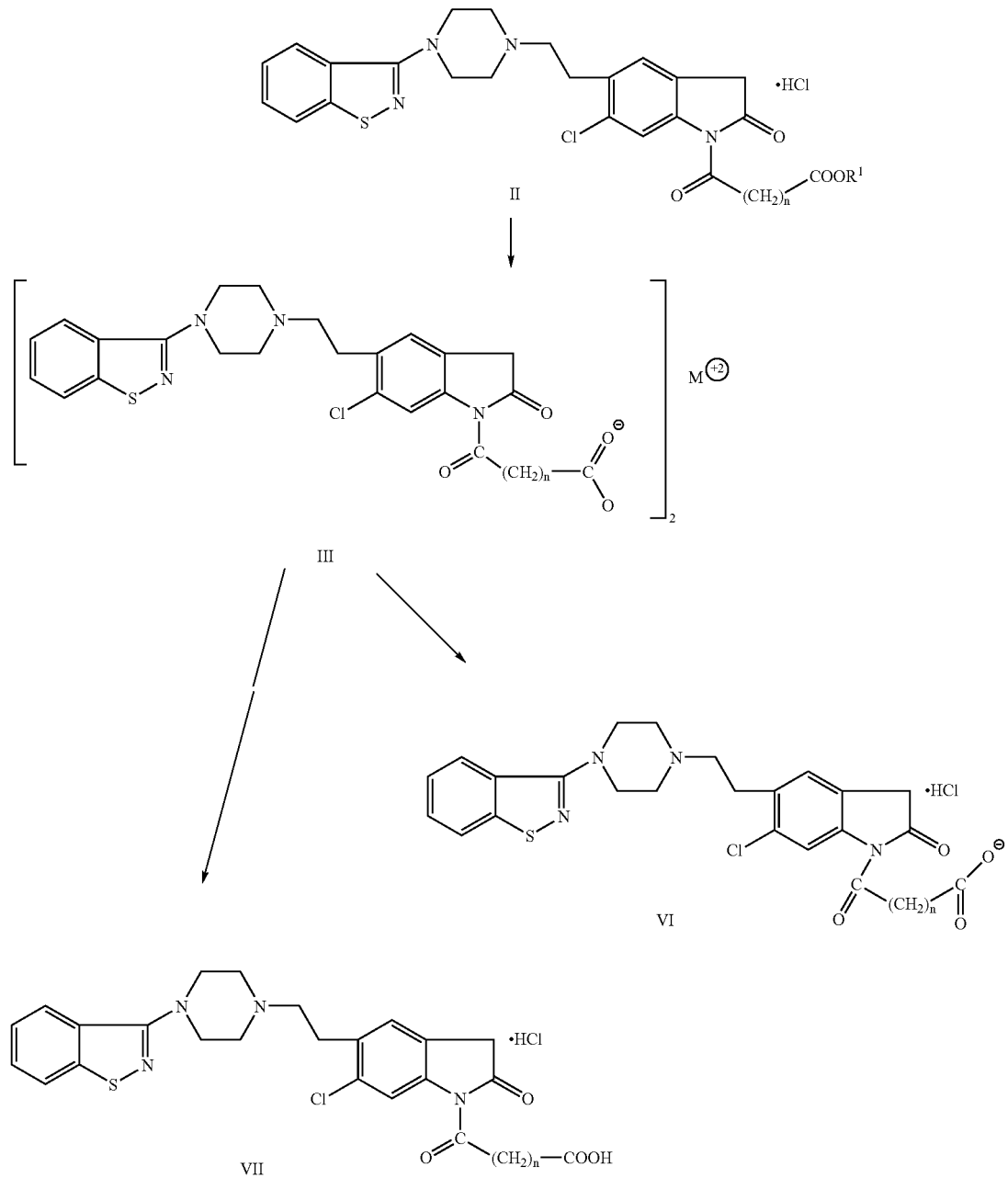

Referring to Scheme 3, the reaction of compound III with a selected alcohol R$^1$OH in hydrochloric acid yields the acyl derivatives of ziprasidone in the chemical form of a half-ester hydrochloride acid salt (II).

Optionally, compound III may be reacted with water and hydrochloric acid to yield a carboxylic acid in the form of zwitterion VI or the hydrochloride acid salt, VII.

Pro-drugs of ziprasidone may be administered as a neuroleptic agent. Administration to a human subject may be alone or, preferably, in combination with pharmaceutically acceptable carriers or diluents in a pharmaceutical composition, in accordance with standard pharmaceutical practice. The pro-drugs of ziprasidone may be administered orally or parenterally including intravenously or intramuscularly. Suitable pharmaceutical carriers include solid diluents or fillers, and sterile aqueous solutions and various organic solvents. The pharmaceutical compositions are then readily administered in a variety of dosage forms, such as tablets, powders, lozenges, syrups, and injectable solutions. These pharmaceutical compositions, if desired, may contain additional ingredients such as flavorings, binders and excipients. Thus, for purposes of oral administration, tablets containing various excipients such as sodium citrate, calcium carbonate and calcium phosphate may be employed along with various disintegrants such as starch, alginic acid, and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers to soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

The effective dosage for the ziprasidone pro-drugs of the present invention depends on the intended route of administration, the indications to be treated, and other factors such as age and weight of the subject. In the following dosage ranges, the term "mgA" refers to milligrams of the free base of the pro-drug. A recommended range for oral dosing is 6 to 400 mgA/day, preferably 50 to 250 mgA/day, more preferably 50 to 100 mgA/day. A recommended range for parenteral administration, such as injection is 3.0 mgA/day to 200 mgA/day and preferably 6.0 to 100 mgA/day.

Because of their improved solubility in water as compared to ziprasidone, the pro-drugs of the present invention may be formulated as parenteral drugs. As another advantage, the present pro-drugs are slowly hydrolyzed in the body; and, therefore release ziprasidone into the patients system gradually over an extended period of time. As a result of this slower rate of availability, the frequency of administration to the patent is desirably reduced. For parenteral administration, a solution or suspension of a pro-drug of ziprasidone in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosage for a pro-drug of ziprasidone depends on the intended route of administration and other factors such as age and weight of the subject, as generally known.

The following Preparations and Examples of the pro-drugs of the present invention are provided solely for the purpose of further illustration and are not intended to limit the scope of the claimed invention. Commercial reagents were utilized without further purification. Melting points are uncorrected. NMR data are reported in parts per million (δ) and are referenced to the deuterium lock signal from the sample solvent. Unless otherwise stated, all mass spectrum were performed using electron impact (EI, 70 eV) conditions. Unless otherwise indicated, chromatography refers to column chromatography performed using 32–63, μm silica gel and executed under nitrogen pressure (flash chromatography) conditions. High Pressure Liquid Chromatography (HPLC) was performed on Hewlett Packard 1100 series HPLC. A Inertsil 5 μ C8 150×4.6 mm (MetaChem, Technologies Inc.) was used for HPLC analysis (mobile phase: 1100 mL Acetonitrile, 1000 mL water, 2 mL H$_3$PO$_4$, 2 mL TEA); Flow Rate of 1.0 mL/min; Detector UV. 250 nm; Injector: 10 uL; column temperature 35 C Preparation 1

Succinic acid 5-[2-(4-benzo[d]isothiazol-3-yl-piperazin-1-yl) ethyl]-6-chloro-1-(3-ethoxycarbonyl-propionyl)-1H-indoyl-2-yl ester ethyl ester Anhydride Formation In Situ Part A:

Ethyl succinyl chloride [ethyl 3-(chloroformyl) proprionate] (57 mL, 381 mmol, 2.5 molar equivalents), was dissolved in anhydrous dichloromethane (610 mL) under a nitrogen atmosphere in the temperature range 15–25° C. Sodium hydroxide pellets (3.1 g, 76 mmol, 0.5 molar equivalents) were then added and the resultant mixture stirred well under nitrogen for 75 min. at 15–25° C. This mixture was then held for use in Part B.

Acylation Reaction

Part B:

Magnesium bromide diethyl etherate adduct, MgBr$_2$.Et$_2$O (82.3 g, 320 mmol, 2.1 molar ratio) was stirred into anhydrous dichloromethane (1200 mL) under a nitrogen atmosphere in the temperature range 15–25° C. The nitrogen atmosphere was maintained for the entire procedure. Triethylamine (54 mL, 3 81 mmol, 2.5 molar ratio) was added and the resultant suspension was cooled to 6.5° C. To the cooled suspension a solution of ziprasidone (63.0 g, 153 mmol, 1 molar ratio) in anhydrous tetrahydrofuran (1100 mL) was added over 20 min. while the reaction mixture temperature was maintained at 6.5° C., when the addition was completed the reaction mixture was stirred for a further 40 min. at 6.5° C. Next the previously prepared solution of anhydride described in Part A was added over a 30 min. period under nitrogen such that atmospheric moisture was not allowed to contact the reagent or reaction mixture. During this addition operation the reaction temperature increased from 6.5° C. to 14° C. After the addition was complete the reaction mixture was stirred for 1 h at 10° C. and 6 h at 15–25° C. The reaction mixture was then quenched by addition of distilled water (1000 mL), the organic layer was separated and the residual aqueous layer extracted twice with dichloromethane (2×250 mL). The dichloromethane layer and extracts were combined and reduced in volume under reduced pressure to about 800 mL. The combined concentrated dichloromethane solution was washed twice with distilled water (2×400 mL), dried over anhydrous sodium sulfate, filtered and evaporated to dryness under reduce pressure to yield 100.6 g of product as a cream brown solid.

Preparation 2

4-{5-[2-(4-benzo[d]isothiazol-3-yl-piperazin-1-yl) ethyl]-6-chloro-2-oxo-2,3-dihydro-indol-1-yl}-4-oxo-butyric acid barium salt The product of Preparation 1 (15.0 g, 22.4 mmol, 1 molar ratio), tetrahydrofuran (112 mL), distilled water (280 mL) and barium hydroxide (12.0 g, 44.8 mmol. 2 molar ratio) were stirred together to form a reaction mixture and stirred for 24 h at 69–71° C. During the reaction period a heavy slurry is formed. When the reaction period is completed the reaction mixture is cooled to 15–30° C. and water (200 mL) added and the quenched reaction mixture stirred for 15 min. The precipitated product was isolated by filtration, washed with distilled water (500 mL) and dried under vacuum to give 29 g of white solids, which is a mixture of barium salt and residual inorganic barium salts. This product is used without further purification in the next step described in Example 3.

Preparation 3

4-{5-[2-(4-benzo[d]isothiazol-3-yl-piperazin-1-yl) ethyl]-6-chloro-2-oxo-2,3-dihydro-indol-1-yl}-4-oxo-butyric acid calcium salt The product of preparation 1 (78.2 g, 116.9 mmol) and 95% pure calcium hydroxide (26.8 g, 140 mmol), tetrahydrofuran (585 mL) and water (1460 mL) were combined together and stirred for 16 hours at 65° C. The resultant reaction mixture was cooled to room temperature and water (600 mL) added. The product started to precipitate and was completed after a period of granulation at room temperature of at least 20 minutes. The resultant calcium salt product was isolated by filtration, washed with water (400 mL) and dried under vacuum at 90° C. for at least 16 hours. This product contains water of hydration and trace impurities.

EXAMPLE 1

Preparation of 4-{5-[2-(4-Benzo[d]isothiazol-3-yl-piperazin-1-yl)-ethyl]-6-chloro-2-oxo-2,3-dihydro-indol-1-yl}-4-oxo-butyric acid ethyl ester, hydrochloride salt The product of Preparation 1 (27.8 g, 53.2 mmol), ethanol (530 mL) and 32% concentrated hydrochloric acid (20 mL, ~4.5 equivalent) were combined together. This mixture was boiled under reflux for 2 hours at 79° C. (Reaction completion was carefully monitored by HPLC product peak observed at ~2.7 min and a possible reaction side product at ~5.3 min.) The reaction mixture was filtered at ~70° C. and the residue washed with hot ethanol (50 mL) at ~70° C. The filtrate and wash were combined and allowed to cool to room temperature. Water (100 mL) was added to initiate crystallization, after a period of granulation of minimum 15 minutes at room temperature the product was isolated by filtration, washed with water (100 mL) and dried for 1 day in a vacuum oven at 75° C. Yield 19.8 g, 64.4% Off-white to reddish pale brown solid.

$C_{27}H_{30}Cl_2N_4O_4S$ requires: C, 56.15; H, 5.24; Cl, 12.28; N, 9.70; S, 5.55. Found: C, 55.51; H, 5.27; Cl, 12.04; N, 9.67; S, 5.28.

FT-IR: 3149, 2954, 2508, 2430, 1728, 1656, 1624, 1590, 1561, 1494, 1474, 1447, 1377, 1351, 1290, 1159, 1038, 1013, 993, 878, 736, 712, 596, 548.

$^1$H-NMR (DMSO, 400 MHz): δ 11.41 (bs), 8.15–8.08 (m), 7.64 (s), 7.58 (t), 7.45 (t,), 6.95 (bs), 4.02 (q), 3.69 (bs), 3.53 (bs), 3.36 (bs), 3.33–3.30 (t,), 3.23–3.21 (m); 2.65 (t), 2.48 (t), 1.15 (t).

$^{13}$C-NMR (DMSO, 400 MHz): δ 172.51, 162.89, 152.81, 128.81, 127.66, 125.33, 124.74, 121.89, 60.79, 55.87; 51.27, 47.20, 28.15, 14.76.

EXAMPLE 2

4-{5-[2-(4-Benzo[d]isothiazol-3-yl-piperazin-1-yl)-ethyl]-6-chloro-2-oxo-2,3-dihydro-indol-1-yl}-4-oxo-butyric acid ethyl ester The compound (15.0 g, 26.0 mmol), from Example 1, dichloromethane (150 mL) and 5% w/v aqueous sodium hydrogen carbonate solution (150 mL) were combined and the resultant mixture was well stirred for 25 min at 35° C. Dichloromethane (100 mL) was then added and stirring was continued for 20 min. at 30° C. The reaction mixture was extracted with dichloromethane (2×100 mL), separated from the aqueous layer and the combined organic layer washed with water (4×200 mL). The washed organic layer was dried over anhydrous sodium sulfate, filtered and concentrated under vacuum to approximately 100 mL. To the concentrate thus obtained acetonitrile (500 mL) was added, crystallization was initiated during this addition, and the resultant crystal slurry further concentrated under vacuum to remove the remainder of the dichloromethane. This solid was filtrated and dried in a vacuum oven at 60° C.

Recrystallization: The initially isolated product was dissolved in the minimum amount of hot dichloromethane and acetonitrile was added until crystallization was initiated and the resultant crystal slurry further concentrated under vacuum to remove the remainder of the dichloromethane. The purified solid was filtrated and dried in a vacuum oven at 60° C.

$C_{27}H_{29}ClN_4O_4S$ requires: C, 59.94; H, 5.40; Cl, 6.55; N, 10.35; S, 5.93. Found: C; 59.66; H, 5.71; Cl, 6.72; N, 10.58; S, 5.97.

FT-IR: 2983, 2839, 2812, 1730, 1657, 1638, 1562, 1490, 1470, 1462, 1422, 1386, 1282, 1263, 1240, 1153, 1121, 1037, 1013, 991, 940, 892, 799, 739, 668, 646, 583.

$^1$H-NMR (DMSO, 400 MHz): δ 8.10–8.05 (m), 7.69 (s), 7.55 (t), 7.43 (t), 6.75 (s), 4.01 (q), 3.59 (s), 3.13–3.08 (m), 2.95 (s), 2.54 (t), 2.48 (s), 1.14 (t).

$^{13}$C-NMR (DMSO, 400 MHz): δ 173.50, 163.54, 152.74, 135.41, 128.68, 128.68, 127.84, 125.21, 124.79, 121.80, 60.41, 58.01, 52.33, 48.93, 31.95, 30.27, 29.88, 14.79.

EXAMPLE 3

4-{5-[2-(4-benzo[d]isothiazol-3-yl-piperazin-1-yl) ethyl]-6-chloro-2-oxo-2,3-dihydro-indol-1-yl}-4-oxo-butyric acid ethyl ester, hydrochloride salt The barium salt produced in Preparation 2, (21.0 g), ethanol (550 mL) and concentrated hydrochloric acid (6 mL) were added together and the resultant reaction mixture was boiled under reflux at 78–80° C. for 4 hr. A further portion of concentrated hydrochloric acid (4 mL) was added to the reaction mixture and the heating under reflux continued for 1 h. Ethanol (1 00 mL) was added to the hot un-cooled reaction mixture and the resultant mixture stirred for 10 min without further cooling. The precipitated barium salts were removed by hot filtration and washed with hot ethanol (200 mL). The ethanol filtrate and washes were combined together and concentrated under reduced pressure. Hexane was added to cloud point until product solids precipitated from solution. The precipitated solids were isolated by filtration and dried under vacuum to yield product, 5.6 g. 65% over two process steps.

EXAMPLE 4

4-{5-[2-(4-benzo[d]isothiazol-3-yl-piperazin-1-yl) ethyl]-6-chloro-2-oxo-2,3-dihydro-indol-1-yl}-4-oxo-butyric acid isobutyl ester, hydrochloride salt The product of Example 3, (1.0 g, 1.7 mmo1, 1 molar equivalent) was dissolved in 2-methyl-1-propanol (27 mL) and concentrated hydrochloric acid (136 µL, 1 molar equivalent) added and the resultant reaction mixture heated in the temperature range 98–100° C. for 4.5 h. The reaction liquor was allowed to cool to room temperature in the range 15–25° C. and distilled water (10 mL) was added after a period of 15 min. granulation the product was isolated by filtration and dried under vacuum. Yield 64 Omg, (62%).

EXAMPLE 5

4-{5-[2-(4-benzo[d]isothiazol-3-yl-piperazin-1-yl) ethyl]-6-chloro-2-oxo-2,3-dihydro-indol-1-yl}-4-oxo-butyric acid methyl ester, hydrochloride salt The product of Preparation 2, (1.0 g), methanol (26 mL) and sufficient concentrated hydrochloric acid were added together until the reaction mixture was acidic by test. The resultant reaction mixture was boiled under reflux at 63–65° C. for 24 h. The reaction mixture was cooled to room temperature in the range 15–25° C. and distilled water (25 mL) added and the mixture stirred for 30 min. in the temperature range 15–25° C. Product solids precipitated from solution, isolated by filtration and dried under vacuum to yield product, 490 mg. (49%).

EXAMPLE 6

4-{5-[2-(4-benzo[d]isothiazol-3-yl-piperazin-1-yl) ethyl]-6-chloro-2-oxo-2,3-dihydro-indol-1-yl}-4-oxo-butyric acid ethyl ester, hydrochloride salt The product of Example 5, (611 mg, 1.1 mmol) was mixed with ethanol (27 mL) and concentrated hydrochloric acid (0.5 mL) and the mixture boiled under reflux for 24 h in the temperature range 78–80° C. Distilled water (20 mL) was added to the hot reaction mixture and solids removed during the hot filtration. The filtrate was cooled further and product solids were isolated by filtration, washed with distilled water (20 mL), and dried under vacuum to yield 200 mg (32%).

EXAMPLE 7

Preparation of 4-{5-[2-(4-Benzo[d]isothiazol-3-yl-piperazin-1-yl)-ethyl]-6-chloro-2-oxo-2,3-dihydro-indol-1-yl}-4-oxo-butyric acid ethyl ester, hydrochloride salt The calcium salt product of preparation 3 (27.8 g, 53.2 mmol), ethanol (530 mL) and 32% concentrated hydrochloric acid (20 mL, ~4.5 equivalent) were combined together and this mixture was boiled under reflux for 2 hours at 79° C. (Reaction completion was carefully monitored by HPLC product peak observed at ~2.7 min and a possible reaction side product at ~5.3 min.) The reaction mixture was filtered at ~70° C. and the residue washed with hot ethanol (50 mL) at ~70° C. The filtrate and wash were combined and allowed to cool to room temperature. Water (100 mL) was added to initiate crystallization, after a period of granulation of minimum 15 minutes at room temperature the product was isolated by filtration, washed with water (100 mL) and dried for 1 day in a vacuum oven at 75° C. Yield 19.8 g, 64.4% Off-white to reddish pale brown solid.

$C_{27}H_{30}Cl_2N_4O_4S$ requires: C, 56.15; H, 5.24; Cl, 12.28; N, 9.70;S, 5.55. Found: C, 55.51; H, 5.27; Cl, 12.04; N, 9.67; S, 5.28.

FT-IR: 3149, 2954, 2508, 2430, 1728, 1656, 1624, 1590, 1561, 1494, 1474, 1447, 1377, 1351, 1290, 1159, 1038, 1013, 993, 878, 736, 712, 596, 548.

$^1$H-NMR (DMSO, 400 MHz): δ 11.41 (bs), 8.15–8.08 (m), 7.64 (s), 7.58 (t), 7.45 (t,), 6.95 (bs), 4.02 (q), 3.69 (bs), 3.53 (bs), 3.36 (bs), 3.33–3.30 (t,), 3.23–3.21 (m), 2.65 (t), 2.48 (t), 1.15 (t).

$^{13}$C-NMR (DMSO, 400 MHz): δ 172.51, 162.89, 152.81, 128.81, 127.66, 125.33, 124.74, 121.89, 60.79, 55.87, 51.27, 47.20, 28.15, 14.76.

EXAMPLE 8

Preparation of 4-{5-[2-(4-Benzo[d]isothiazol-3-yl-piperazin-1-yl)-ethyl]-6-chloro-2-oxo-2,3-dihydro-indol-1-yl}-4-oxo-butyric acid ethyl ester The product of example 1 or example 7 (15.0 g, 26.0 mmol), dichloromethane (150 mL) and 5% w/v aqueous sodium hydrogen carbonate solution (150 mL) were combined and the resultant mixture was well stirred for 25 min at 35° C. Dichloromethane (100 mL) was then added and stirring was continued for 20 min. at 30° C. The reaction mixture was extracted with dichloromethane (2×100 mL), separated from the aqueous layer and the combined organic layer washed with water (4×200 mL). The washed organic layer was dried over anhydrous sodium sulfate, filtered and concentrated under vacuum to approximately 100 mL. To the concentrate thus obtained acetonitrile (500 mL) was added, crystallization was initiated during this addition, and the resultant crystal slurry further concentrated under vacuum to remove the remainder of the dichloromethane. This solid was filtrated and dried in a vacuum oven at 60° C.

Recrystallization: The initially isolated product was dissolved in the minimum amount of hot dichloromethane and acetonitrile was added until crystallization was initiated and the resultant crystal slurry further concentrated under vacuum to remove the remainder of the dichloromethane. The purified solid was filtrated and dried in a vacuum oven at 60° C.

$C_{27}H_{29}ClN_4O_4S$ requires: C, 59.94; H, 5.40; Cl, 6.55; N, 10.35; S, 5.93. Found: C, 59.66; H, 5.71; Cl, 6.72; N, 10.58; S, 5.97.

FT-IR: (cm$^{-1}$) 2983, 2839, 2812, 1730, 1657, 1638, 1562, 1490, 1470, 1462, 1422, 1386, 1282, 1263, 1240, 1153, 1121, 1037, 1013, 991, 940, 892, 799, 739, 668, 646, 583.

$^1$H-NMR (DMSO, 400 MHz): δ 8.10–8.05 (m), 7.69 (s), 7.55 (t), 7.43 (t), 6.75 (s), 4.01 (q), 3.59 (s), 3.13–3.08 (m), 2.95 (s), 2.54 (t), 2.48 (s), 1.14 (t).

$^{13}$C-NMR (DMSO, 400 MHz): δ 173.50, 163.54, 152.74, 135.41, 128.68, 128.68, 127.84, 125.21, 124.79, 121.80, 60.41, 58.01, 52.33, 48.93, 31.95, 30.27, 29.88, 14.79.

EXAMPLE 9

4-{5-[2-(4-Benzo[d]isothiazol-3-yl-piperazin-1-yl)-ethyl]-6-chloro-2-oxo-2,3-dihydro-indol-1-yl}-4-oxo-butyric acid, hydrochloride salt The calcium salt product of preparation 3 (20 g, 37.6 mmol) and concentrated hydrochloric acid (7.9 mL, 2.5 equivalent), and water (750 mL) were combined together and stirred overnight at 50° C. The resultant reaction mixture was a slurry, it was cooled to room temperature and water (250 mL) added. The product was granulated at room temperature for at least 10 minutes. The resultant product was isolated by filtration, washed with water (100 mL) and dried under vacuum at 90° C. for at least 16 hours. Yield 15.2 g, 74% Off-white to light brown solid.

$^1$H-NMR (DMSO, 400 MHz): δ 10.24 (bs), 9.55 (bs), 8.07–8.03 (m), 7.73 (s), 7.55 (t), 7.42 (t,), 7.27(bs), 6.84 (bs), 6.63 (bs), 3.47 (bs), 3.20 (bs), 2.95–2.84 (m), 2.73 (bs), 2.59 (bs), 2.49 (bs), 2.39 (bs).

EXAMPLE 10

4-{5-[2-(4-Benzo[d]isothiazol-3-yl-piperazin-1-yl)-ethyl]-6-chloro-2-oxo-2,3-dihydro-indol-1-yl}-4-oxo-butyric acid, mesylate salt The calcium salt product of preparation 3 (10 g, 19.5 mmol), tetrahydrofuran (75 mL, water (75 mL), and methane sulfonic acid (9.5 mL, 7.5 eqvvialent) were combined together and stirred overnight at ambient temperature. The resultant product was isolated by filtration, washed with thf/water (30 mLs) and dried under vacuum at 45° C. for at least 16 hours. Yield 5.4 g, 54%. Off-white to light brown solid.

$^1$H-NMR (DMSO, 300 MHz): δ 9.85 (bs), 8.20–8.12 (m), 7.65–7.60 (m), 7.50 (t), 6.98 (bs), 4.17 (d), 3.84–3.73 (m), 3.50–3.33 (m), 3.24–3.12 (m), 2.63–2.57 (m), 2.53–2.50 (m), 2.43 (s), 2.35 (s), 2.09 (s), 1.36 (s).

EXAMPLE 11

Preparation of 4-{5-[2-(4-Benzo[d]isothiazol-3-yl-piperazin-1-yl)-ethyl]-6-chloro-2-oxo-2,3-dihydro-indol-1-yl}-4-oxo-butyric acid decyl ester, hydrochloride salt The product of example 9 (4.0 g, 7.28 mmol), 4-dimethylaminopyridine (800 mg, 6.55 mmol, 0.9 equivalent), N,N"dicyclohexylcarbodiimide (2.0 g, 9.46 mmol, 1.3 equivalent) and dichloromethane (25 mL) were aded together to form a dark solution. Then 1-decanol (1.5 mL, 8.0 mmol, 1.1 equivalent) was added to the dark solution obtained above. The resultant reaction mixture was heated to 40° C. for 3 days. The product was isolated by adding dichloromethane (40 mL) and water (20 mL) to the reaction mixture. The organic layer was separated and further washed with water (2×20 mL) The washed organic layer was dried over anhydrous sodium sulfate, filtered and concentrated to dryness in a vacuum rotary evaporator. The resultant black gum (6.43 g) was dried in vacuum oven overnight.

Purification By Column Chromatography:

Stationary phase: Silica Gel 60 A, mobile phase: ethyl acetate

Fraction 1 to 7 were collected and concentrated to approximate 50 mL of ethyl acetate by rotary evaporation. Hexanes were added until solids precipitate. Granulate for 4 h and filter. Wash solids with 50 mL of hexanes. Dry filtrated solids on a vacuum oven at 80 C for 18 h. This afforded the product (2.3 g) as a purple brown fine solids.

FT-IR (cm$^{-1}$): ν 3320, 2924, 2850, 1724, 1609, 1473, 1454, 1420, 1381, 1350, 1258, 1162, 1024, 907, 863, 735, 703, 666, 584.

$^1$H-NMR (DMSO, 400 MHz): δ 10.29 (bs), 8.04 (d), 7.70 (bs), 7.54 (t), 7.41 (t,), 7.25(bs), 7.19 (s) 6.82 (bs), 6.62 (bs), 5.58 (d), 3.93 (bs), 3.47 (s), 3.35 (bs), 2.99–2.96 (m), 2.87 (bs), 2.73 (bs), 2.62 (bs), 2.49 (s), 1.71 (d), 1.59 (d), 1.49 (bs), 1.17 (bs), 0.81 (t).

We claim:

1. A compound of the formula

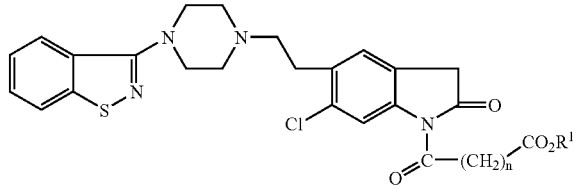

I or a pharmaceutically acceptable acid addition salt thereof wherein $R^1$ is selected from the group consisting of hydrogen and alkyl $C_1$ to $C_{10}$; and wherein n is an integer from 1 to 5.

2. A compound according to claim 1 wherein $R^1$ is ethyl.

3. A compound according to claim 1 wherein said pharmaceutically acceptable acid addition salt is selected from the group consisting of chloride, mesylate, acetate, fumarate, succinate, maleate, besylate, citrate, tartrate and sulfate.

4. A compound according to claim 3 wherein said pharmaceutically acceptable acid addition salt is the hydrochloride salt.

5. A compound according to claim 3 wherein said pharmaceutically acceptable acid addition salt is the mesylate salt.

6. A compound according to claim 1, wherein said compound is 4-{5-[2-(4-benzo[d]isothiazol-3-yl-piperazin-1-yl)-ethyl]-6-chloro-2-oxo-2,3-dihydro-indol-1-yl}-4-oxo-butyric acid ethyl ester, hydrochloride salt.

7. A process for preparing a compound of formula

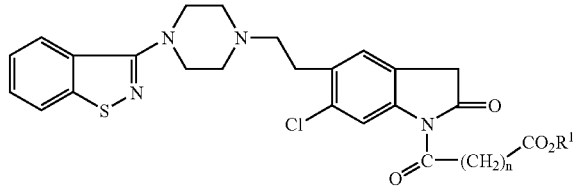

I comprising reacting a compound of formula

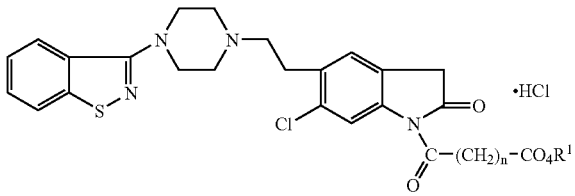

II with a base wherein $R^1$ is selected from the group consisting of hydrogen and alkyl $C_1$ to $C_{10}$; and wherein n is an integer from 1 to 5.

8. The process of claim 7 wherein said compound of formula II is prepared by reacting a compound of the formula

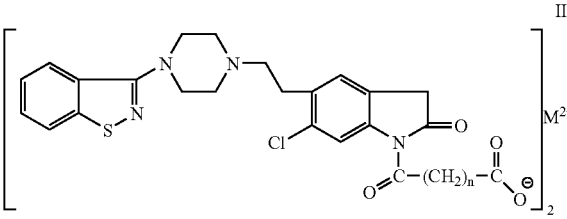

III with an alcohol of formula $R^1OH$ in the presence of concentrated hydrochloric acid wherein M is Ca or Ba; and $R^1$ is selected from the group consisting of hydrogen and alkyl $C_1$ to $C_{10}$; and wherein n is 1 to 5.

9. The process of claim 8 wherein said compound of formula III is prepared by reacting a compound of formula

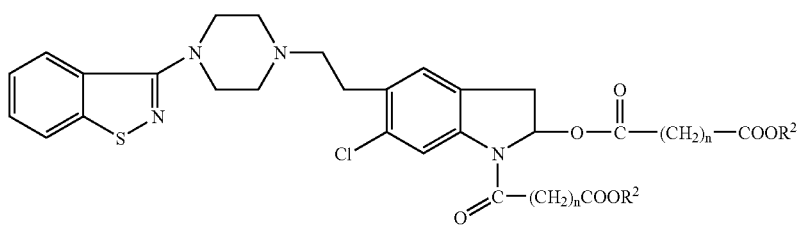

IV with calcium hydroxide or barium hydroxide wherein $R^2$ is $C_1$–$C_{10}$ alkyl and n is an integer from 1 to 5.

10. The process of claim 9 wherein said compound of formula IV is prepared by reacting a compound of formula

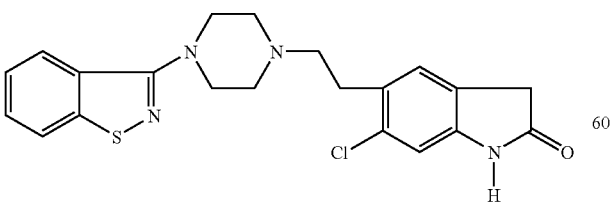

V with an anhydride acylating agent.

11. The process of claim 10 wherein said acylating agent is an anhydride acylating agent having the formula

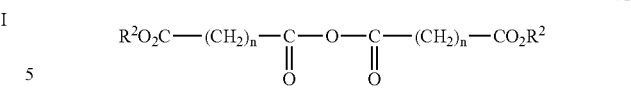

VI wherein $R^2$ is $C_1$–$C_{10}$ alkyl and n is an integer from 1 to 5.

12. The process of claim 10 wherein said anhydride acylating agent reacts with the compound of formula V in the presence of magnesium bromide-diethyl ether etherate and an organic base.

13. The process of claim 11 wherein said anhydride acylating agent is the anhydride having the formula

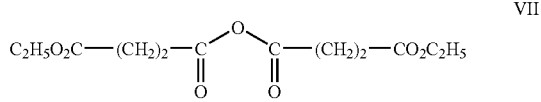

VII

14. The process of claim 12 wherein said organic base is triethylamine.

15. The process of claim 7 wherein said base is selected from the group consisting of alkali metal bicarbonates, alkali metal carbonates, C-1 to C-6 trialkylamines; and heterocyclic bases selected from the group consisting of pyridine, lutidine and picoline.

16. The process of claim 15 wherein said base is sodium bicarbonate.

17. A pharmaceutical composition having neuroleptic activity comprising the compound according to claim 1 in an amount effective in the treatment of neuroleptic diseases, and a pharmaceutically acceptable carrier.

18. A method of treating neuroleptic diseases which comprises administering to a subject in need of such treatment a neuroleptic active amount of the compound according to claim 1.

19. A method of treating neuroleptic diseases according to claim 18, wherein said neuroleptic active amount is an oral dosage in the amount of about 6 mgA per day to about 400 mgA per day.

20. A method according to claim 19 wherein said oral dosage is about 50 mgA per day to about 100 mgA per day.

21. A method of treating neuroleptic disease according to claim 18, wherein said neuroleptic active amount is a parenteral injection in the amount of about 30 mgA per day to about 200 mgA per day.

22. The method according to claim 21 wherein said amount is about 6.0 mgA per day to about 100 mgA per day.

23. A compound of formula

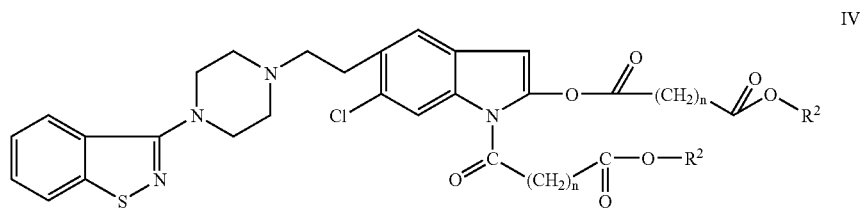

IV or a pharmaceutically acceptable acid addition salt thereof wherein $R^2$ is $C_1$–$C_{10}$ alkyl and n is an integer from 1 to 5.

24. A compound according to claim 23 wherein said compound is succinic acid 5-[2-(4-benzo[d]isothiazol-3-yl-piperzin-1-yl) ethyl]-6-chloro-1-(3-ethoxycarbonyl-propionyl)-1H-indoyl-2-yl ester ethyl ester.

25. A compound of the formula

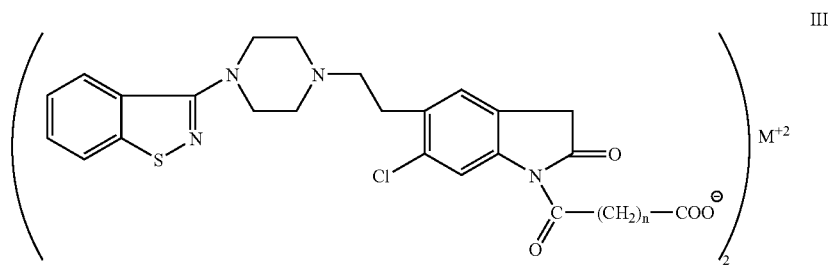

III wherein M is Ca or Ba and n is an integer from 1 to 5.

26. A compound according to claim 25 wherein said compound is 4-{5-[2-(-benzo[d]isothiazol-3-yl-piperzin-1-yl)ethyl]-6-chloro-2-oxo-2,3-dihydroindol-1-yl}-4-oxo-butyric acid calcium salt.

27. A compound according to claim 25 wheein said compound is 4-{5-[2-(4-benzo[d]isothiazol-3-yl-piperazin-1-yl)ethyl]-6-chloro-2-oxo-2,3-dihydro-indol-1-yl}-4-oxo-butyric acid barium salt.

* * * * *